United States Patent [19]
Stoppini et al.

[11] Patent Number: 5,958,762
[45] Date of Patent: Sep. 28, 1999

[54] CELL CULTURE DEVICE

[75] Inventors: Luc Stoppini, Geneve, Switzerland; Philippe Correges, Lugrin, France

[73] Assignee: Chemodyne S.A., Switzerland

[21] Appl. No.: 08/793,496

[22] PCT Filed: Jun. 5, 1996

[86] PCT No.: PCT/IB96/00559
§ 371 Date: Feb. 12, 1997
§ 102(e) Date: Feb. 12, 1997

[87] PCT Pub. No.: WO97/00314
PCT Pub. Date: Jan. 3, 1997

[30] Foreign Application Priority Data

Jun. 15, 1995 [FR] France ................................. 95/07126

[51] Int. Cl.$^6$ ........................................... C12M 3/00
[52] U.S. Cl. ................................. 435/297.5; 435/305.1; 435/305.2
[58] Field of Search ............... 435/297.5, 283.1, 435/288.3, 288.4, 305.1, 305.2

[56] References Cited

U.S. PATENT DOCUMENTS

| | | | |
|---|---|---|---|
| 4,917,793 | 4/1990 | Pitt et al. | 210/94 |
| 4,963,490 | 10/1990 | Churchouse et al. | 435/297.1 |
| 5,462,874 | 10/1995 | Wolf et al. | 435/297.5 |
| 5,602,028 | 2/1997 | Minchinton | 435/401 |

FOREIGN PATENT DOCUMENTS 39 23 279 A1  1/1990  Germany .................. C12M 3/00

*Primary Examiner*—David A. Redding
*Attorney, Agent, or Firm*—Bierman, Muserlian and Lucas

[57] ABSTRACT

A device for culturing dissociated cultures or organotypic cultures on pieces of pre-cut membrane comprising discs of membrane which are circled by a plastic ring provided with a tab and the patch of membrane which is placed in a culture medium selected from the group consisting of in a culture insert, on a semi-solid medium and on the membrane of a box, consisting of a case made of transparent plastic material formed by two assembled parts which are hermetically sealed, the lower part being separated into two compartments by a permeable membrane defining a lower compartment which serves as a reservoir for the culture medium and an upper compartment intended to receive one or more circled membrane discs or eyelets, serving as the site for the cell culture and its use.

14 Claims, 5 Drawing Sheets

CELL CULTURE DEVICE

FIELD OF THE INVENTION

This invention relates to a novel device which allows the culture of dissociated cells or organotypic cultures i.e. that of tissular explants on pieces of membrane which have been cut in advance.

STATE OF THE ART

A method described by LStoppini (J. of Neuroscience Method 37 (1991) p. 173) has already been disclosed, in which slices of nervous tissue from rat hippocampus were kept under culture at the interface between the air and a culture medium. The slices, placed on a sterile, transparent and porous membrane (culture insert), were kept in a Petri dish placed in an incubator. Histological and electrophysiological studies made it possible to evidence that this technique allowed explants to be kept alive and that a tissular organisation close to that which can be found in vivo, is retained.

SUMMARY OF THE INVENTION

This invention relates to the use of discs of membrane which have been pre-cut for the organotypic cultures of slices of tissues obtained from the central nervous system.

The disposition of cultures directly on a membrane of an insert has been found during the use, to display some inconveniences which need to be remedied. In fact, in many applications it is then necessary to be in a position to dispose of tissue outside the insert of the culture. It is needed to cut off the membrane around the issue by means of a scalpel.

During this operation, tissues are often damaged. Morever when someone uses the culture inserts, it is not possible to study each implant individually, which has often resulted in a loss of previously cultured tissue.

To remedy these difficulties and to facilitate the handling of organotypic cultures, a novel support has been developed which is constituted of pieces of membrane which are pre-cut and sterile, and which may be circled with a plastic ring.

Thus, the cell cultures are completely localized on the circled discs, so they can develop autonomously and can be removed or replaced at different times.

A more specific subject of the invention is a new device which enables dissociated cells or organotypic cultures, that is to say tissular explants, to be cultured on pieces of membrane cut up in advance.

These pieces of membrane may be uncircled or circled with a ring of rigid or flexible plastic material (eyelet).

Typically, the eyelets are formed by a ring of plastic having a diameter of 3 to 25 mm and a thickness of 0.1 to 1 mm, onto which a permeable culture membrane, commercially-available, such as those sold under the trade names Millicell or Falcon or Millipore or Membrane Anopore (Whatman), is welded or glued. Thus, it is possible to stretch sufficiently the membrane to facilitate the manipulations and treatments necessary in electron microscopy, light-optical microscopy, electrophysiology and for biochemical studies or measurements.

These discs, circled or uncircled, are prepared in advance and are presented in ready-to-use, individual sterile packages.

These discs may be placed:

1. On standard culture inserts, normally commercially available.
2. On semi-solid medium (like agarose) in Petri dishes.
3. Or they are specially designed or placed in boxes specially designed to hold several discs, disposed on the median membrane, thus forming what is designated hereafter by the term nursery.

The semi-solid medium has for instance the following composition : (MEM 50%, horse serum 25%, Hank's solution 25%, agarose 0.8–1%). the pH balance is obtained either with bicarbonate and 5% $CO_2$ or HEPES (no need of $CO_2$).

The eyelets are deposited on the surface of the semi-solid medium and thus may be kept for several weeks without any need of changing the culture medium. The eyelets may also be deposited on a removable perforated holder allowing all eyelets to be removed in one operation.

In the device according to this invention, the lower compartment of the nursery contains a membrane which, by capillarity, allows the irrigation of one or more cell cultures, placed on the circled discs in a horizontal position on the permeable membrane, in order to be maintained and their development to be brought about.

The cell cultures placed on these discs can be irrigated in spite of the two thicknesses of membrane, that is to say the membrane of the nursery or the conventional culture well, and the membrane of the eyelet. The membrane is transparent and its pore size ranges from 0.02 to 10 $\mu$m.

Two sterile septa are arranged in the lower compartment allowing the perfusion of a nutritive medium. This compartment is provided with sealable openings intended to let the perfusion liquid enter from one side and leave through the other side.

The perfusion of the nutritive medium takes place either by means of an external peristaltic pump or by a peristaltic pump integrated with the nursery case. The reservoir containing the nutritive medium may be, in the same manner, either independent (external), or be part of the nursery.

Specifically, this invention has as a subject matter, a device for cell cultures constituted by a transparent plastic box formed by two assembled parts which can be hermetically sealed, the lower part of which is separated into two compartments by a permeable membrane defining a lower compartment which serves as a reservoir for the culture medium and an upper compartment receiving one or more discs or eyelets serving as the site of the cell culture.

The openings may be connected with each other, such that it is possible to arrange several devices according to the invention, in series, the outlet of one being connected to the inlet of another device. In this way, it is possible to perfuse simultaneously identical or different cell cultures with a same culture medium.

The case of the device can be hermetically sealed while having an opening for the admission or discharge of a gaseous mixture (for example, 5% $CO_2$ in air). For this purpose it may be contemplated to dispose a sealable valve or vent. The inert gas diffuses across a membrane placed in the cover or via a system of baffles.

One of the important characteristics of this invention lies in the fact that the cell cultures are placed on one or more discs (eyelet) provided with a permeable membrane and that these discs are themselves arranged on the permeable membrane which forms the separation between the lower compartment and the upper compartment of the box.

In this way, the nutritive medium bathes the separation membrane, diffuses by capillarity across the latter and finally impregnates said circled discs in order to keep the cell cultures alive.

The cell cultures are therefore carried out on pre-cut permeable pieces of membrane, of standard size.

Figure 1:
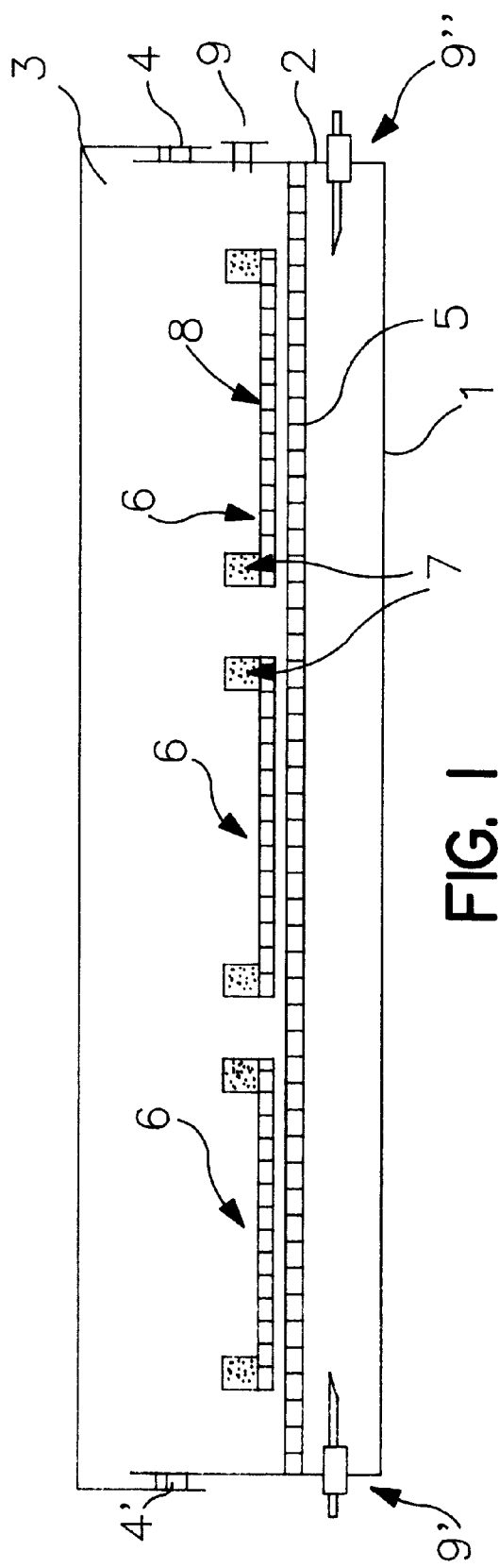
FIG. 1 is a cross section of a device of the invention

In a preferred embodiment of the invention, the device is presented as shown in FIG. 1, in the form of a transparent case (1) of rigid material, formed by a lower part (2) and a fitted cover (3) provided with sealing devices (4) (4'). The lower part of the case has a permeable membrane (5) across it, extended between two opposite sidewalls on which one or more circled discs (6) formed by a rigid ring (7), encircling a permeable membrane surface (8), rest. As a function of the requirements and dimensions of the case, the number of circled discs may vary. In the device represented on FIG. 1, three circled discs are arranged on the permeable membrane (5), constituting together with the box, the nursery.

The case contains in its lower part an inlet nozzle (9') and an outlet nozzle (9") allowing the circulation of the culture medium.

In the upper part a vent (9) allows the introduction of gas during the culture.

Figures 1, 2A:
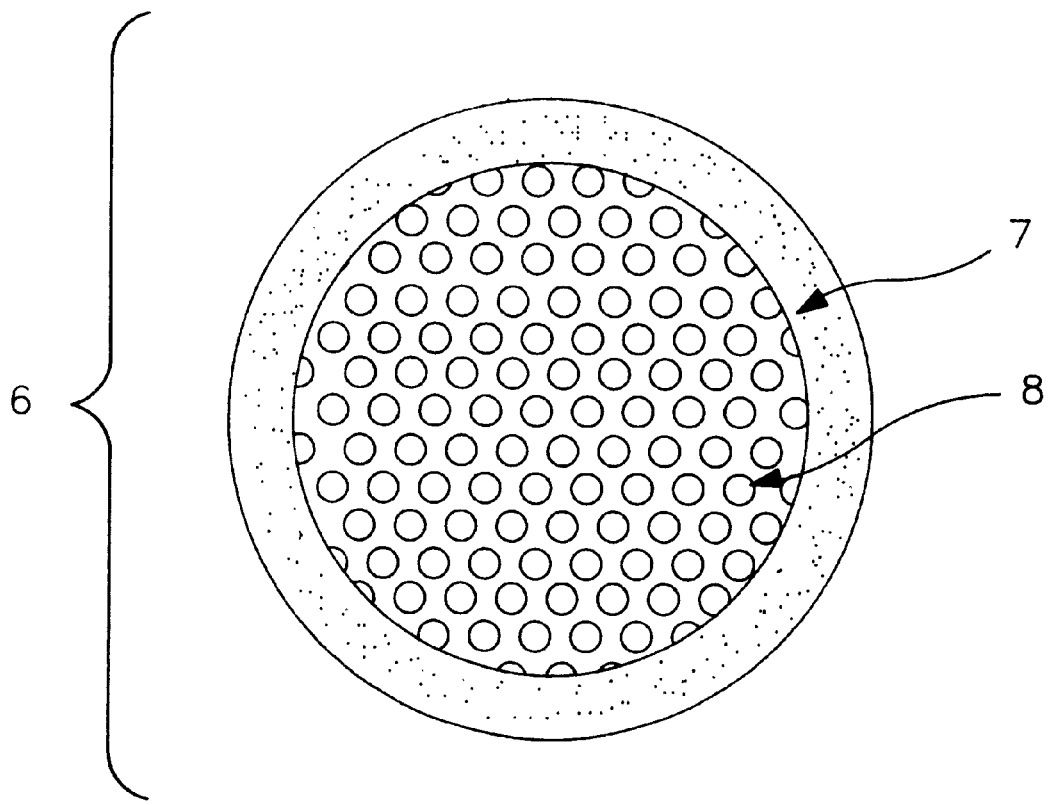
Figures 2, 2A:
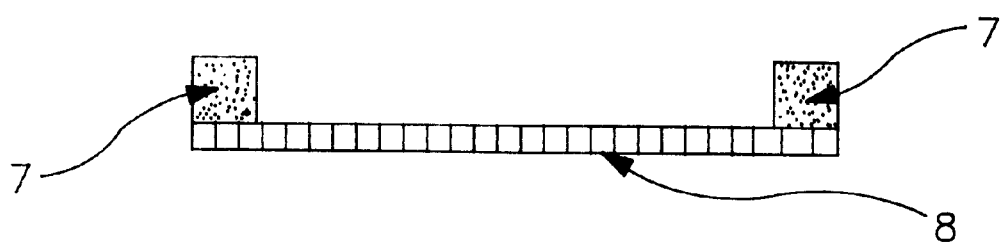
FIG. 2 is a cross section of a rigid ring encircling a permeable membrane surface
Figures 1, 2B:
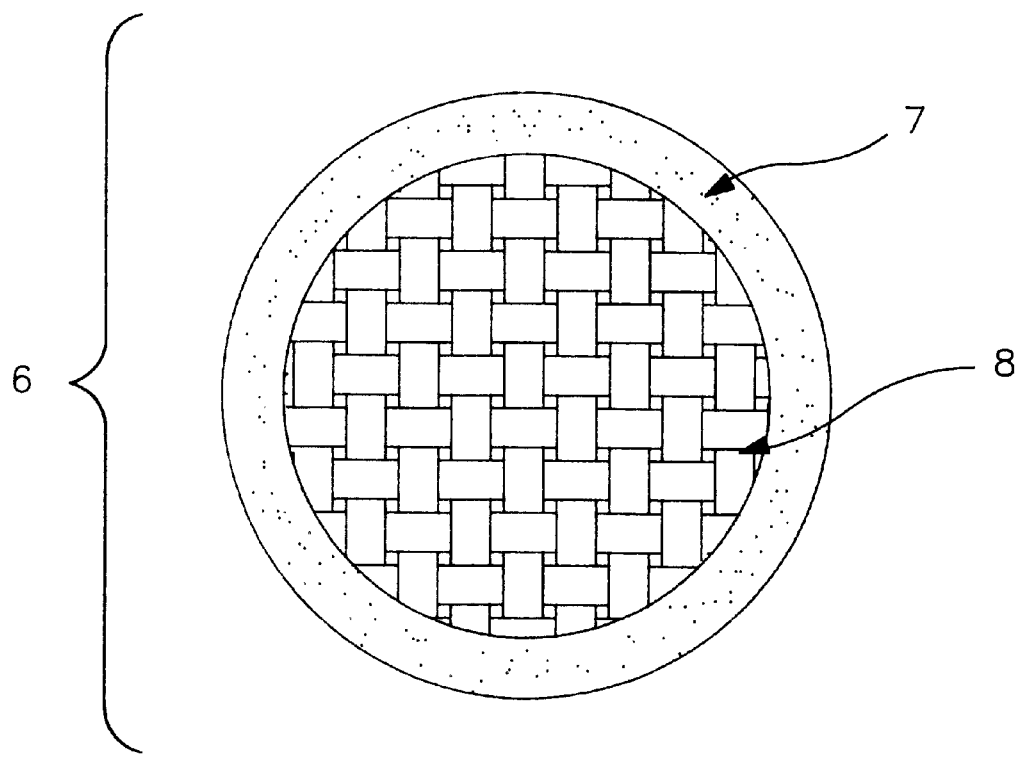
Figures 2, 2B:
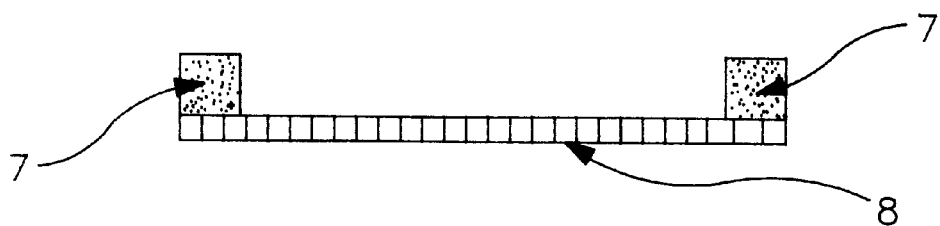

FIGS. 2A and 2B show, seen from above, the circled disc (6) surrounded by the plastic holding ring (7) and, seen in profile, the membrane (8) of the circled disc (6). The membrane may be perforated or formed as a web.

Figure 3A:
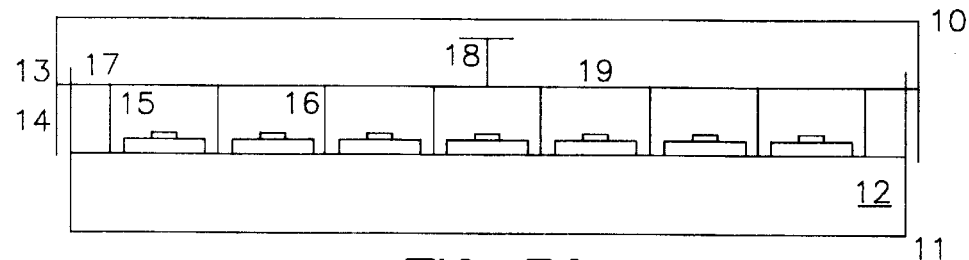
FIG. 3 is a cross section of FIG. 2
Figure 3B:
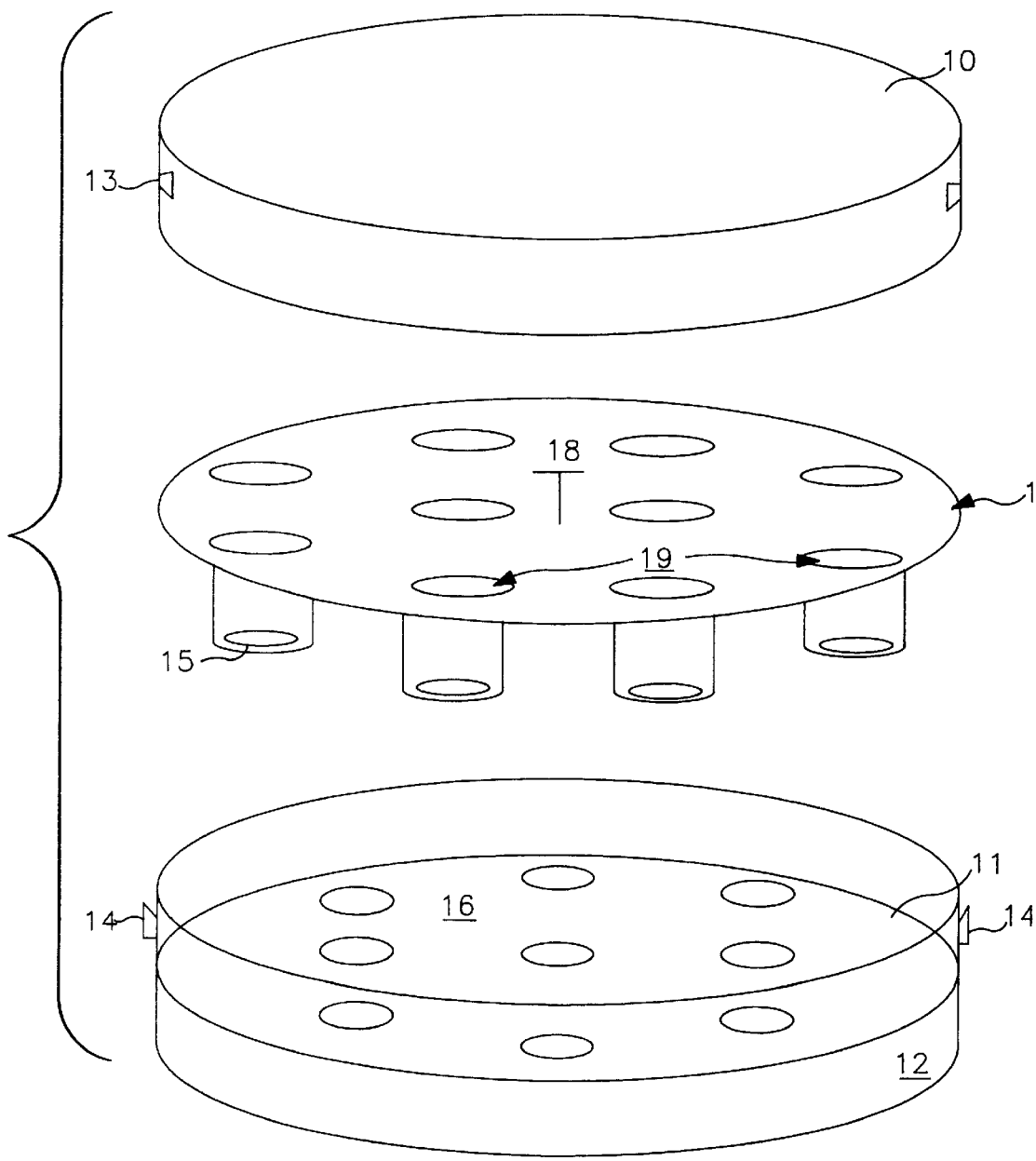

FIG. 3 is a description of the Petri dishes filled with a semi solid medium containing Agarose. The cover of the Petri dish can be seen (10) with a schematized representation of the lock system (13). At the bottom appears the base of the Petri dish with the closure (14) also schematically represented. The lower part of the Petri dish (11) contains the medium.

The figure also represents the discs (15) of membrane with the tissue placed on the medium (16) or directly placed on Agarose (12).

The perforated holder (17) contains several discs (15), a handle (18) and a number of wells (19).

Figure 4:
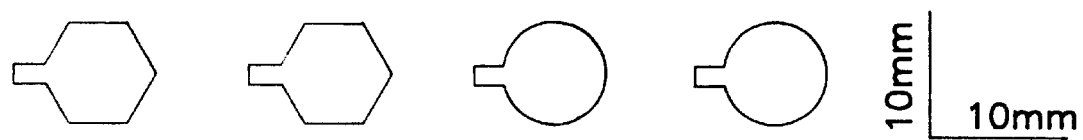
FIG. 4 is an illustration of various membrane provided with a tab for handling uncircled sheets of membrane.

FIG. 4 shows discs of various shapes and including a tab for handling of the disc.

The device according to this invention has, by comparison with existing systems, the following advantages:

The ease of handling.

The cutting of the cell culture, which has grown on the membranes for subsequent treatments, is avoided.

The possibility of carrying out individual removals of tissue, which is not possible in the case of standard wells.

The possibility, in the case of contamination of the well, of replacing the eyelet in a clean well.

The saving of time, more precisely when one utilizes a semi-solid medium because in these conditions the culture may be kept for several weeks without the need to change the culture medium.

The eyelets may be directly placed in a device for electrophysiological measurements such as that designated as Physiocard (french patent application 95.04410 of Apr. 12, 1995).

Economy of cells because on the same total cell surface, it will be possible to carry out different tests.

What is claimed is:

1. A device for culturing dissociated cultures or organotypic cultures on pieces of pre-cut membrane comprising discs of membrane which are optionally circled by a plastic ring and the discs of membrane are placed in a culture medium for living cells on a a permeable membrane of a box consisting of a housing made of transparent plastic material formed by two assembled parts which can be hermetically sealed, the lower part being divided into two compartments by the permeable membrane defining a lower compartment which serves as a reservoir for the culture medium and an upper compartment to receive one or more circled membrane discs or eyelets serving as the site for the cell culture.

2. A device of claim 1 wherein the culture medium is a semi-solid culture medium placed in a Petri dish.

3. A device of claim 1 wherein the discs are irrigated by capillarity of the culture medium through the permeable membrane.

4. A device of claim 1 wherein the discs of membrane are placed onto a perforated holder, allowing irrigation by capillarity of the culture of cells with the culture medium and the removal of one or more discs in one operation.

5. A device of claim 1 wherein the permeable membrane of the box permits irrigation by capillarity of the cell cultures by the culture medium.

6. A device of claim 1 wherein the membranes become transparent when wetted with the culture medium.

7. A device of claim 1 wherein the membranes have a pore size ranging from 0.02 to 10 $\mu$m.

8. A device of claim 1 wherein the circled discs are made of a piece of transparent membrane fixed on a ring of rigid or flexible plastic material.

9. A device of claim 1 wherein the circled discs are made of a ring of plastic material having a thickness of 0.1 to 2 mm and an outside diameter of 3 to 25 mm.

10. A device of claim 1 wherein the permeable membrane is fixed to the ring plastic material by welding or gluing.

11. A device of claim 1 wherein the dics of membrane are pre-cut in any geometrical form and when uncircled by a ring are provided with a tab for holding.

12. A device of claim 1 wherein the lower compartment of the box is provided with an inlet and an outlet for circulation of the culture medium.

13. A device of claim 1 wherein the upper compartment of the box is provided with a valve allowing the introduction of a current of gas and the discharge of said current gas.

14. A method of culturing dissociated cells or organotypic cultures on a sterile medium wherein the culturing step is effected in a device of claim 1.

* * * * *